United States Patent
Jain

(10) Patent No.: US 8,175,723 B2
(45) Date of Patent: *May 8, 2012

(54) STEROID ELUTING PACING TIP ELECTRODE

(75) Inventor: Ravi Jain, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 55 days.

This patent is subject to a terminal disclaimer.

(21) Appl. No.: 12/505,226

(22) Filed: Jul. 17, 2009

(65) Prior Publication Data

US 2009/0281606 A1    Nov. 12, 2009

Related U.S. Application Data

(62) Division of application No. 11/403,257, filed on Apr. 12, 2006, now Pat. No. 7,584,005.

(51) Int. Cl.
*A61N 1/00* (2006.01)

(52) U.S. Cl. .......................................................... 607/120

(58) Field of Classification Search .................... 607/120
See application file for complete search history.

(56) References Cited

U.S. PATENT DOCUMENTS

| | | |
|---|---|---|
| 4,712,555 A | 12/1987 | Thornander et al. |
| 4,788,980 A | 12/1988 | Mann et al. |
| 4,919,135 A | 4/1990 | Phillips, Jr. et al. |
| 4,940,052 A | 7/1990 | Mann et al. |
| 4,944,298 A | 7/1990 | Sholder |
| 5,466,254 A | 11/1995 | Helland |
| 5,476,483 A | 12/1995 | Bornzin et al. |
| 5,477,856 A | 12/1995 | Lundquist |
| 6,198,973 B1 * | 3/2001 | Doan et al. .................... 607/120 |
| 7,389,148 B1 | 6/2008 | Morgan |
| 2002/0147488 A1 | 10/2002 | Doan et al. |

OTHER PUBLICATIONS

NonFinal Office Action, mailed Nov. 28, 2008: U.S. Appl. No. 11/403,257.
NonFinal Office Action (Restriction), mailed Apr. 23, 2009: U.S. Appl. No. 11/403,257.
Notice of Allowance, mailed Jul. 6, 2009: U.S. Appl. No. 11/403,257.

* cited by examiner

*Primary Examiner* — Eric D. Bertram
*Assistant Examiner* — Elizabeth K So

(57) ABSTRACT

An implantable cardioverter defibrillator (ICD) including a set of leads having electrodes disposed therein. The electrodes may include a weld electrode connected to an internal wire of the lead and the ICD and a tip electrode. The tip electrode may have a set of grooves or cut out regions in its outer surface to provide edge effects for currents applied through the tip electrode. The grooves or cut out regions may form gaps in the surface of the tip electrode exposing a medical compound that is housed within the tip electrode. The medical compound may elute through the gaps.

2 Claims, 4 Drawing Sheets

FIG. 5
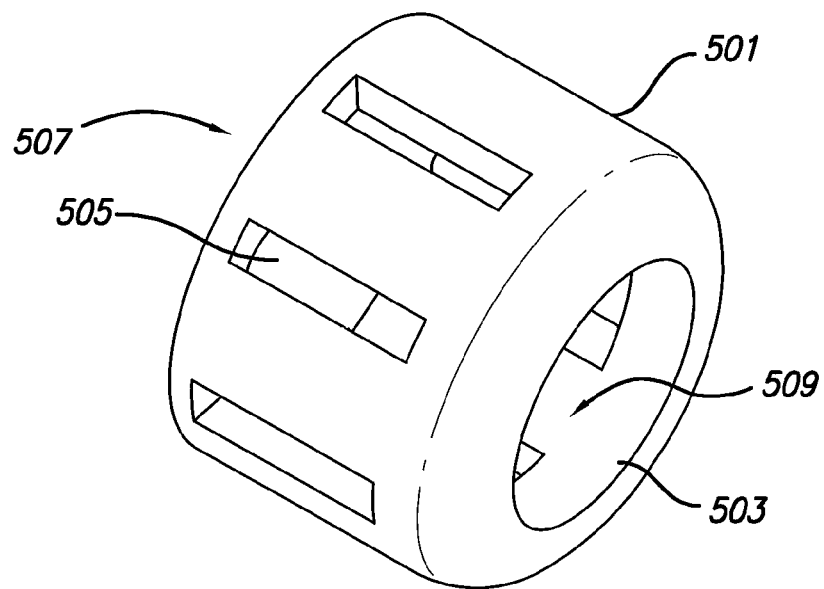
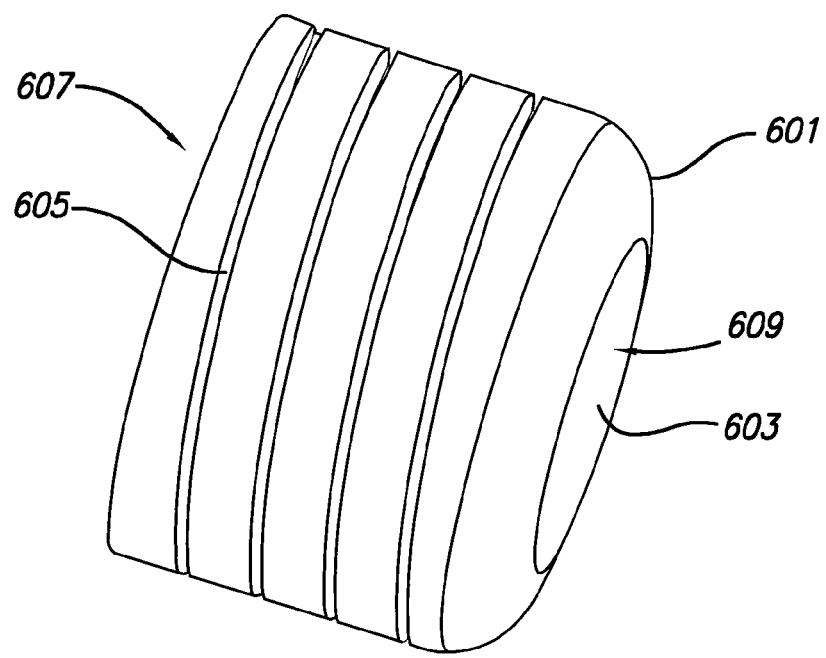
FIG. 6

STEROID ELUTING PACING TIP ELECTRODE

CROSS-REFERENCE TO RELATED APPLICATIONS

This application is a division of U.S. patent application Ser. No. 11/403,257 (now U.S. Pat. No 7,584,005), filed Apr. 12, 2006, titled "STEROID ELUTING PACING TIP ELECTRODE."

TECHNICAL FIELD

The application relates generally to implantable cardiac stimulation devices, and more particularly relates to an electrode tip for a lead to be used for pacing, cardioversion and defibrillation.

BACKGROUND

Implantable cardiac devices are well known in the art. They may take the form of implantable defibrillators or cardioverters, which treat accelerated rhythms of the heart such as fibrillation or implantable pacemakers, which maintain the heart rate within a prescribed limit, such as, for example, to treat a bradycardia. Implantable cardiac devices are also known which incorporate both a pacemaker and a defibrillator.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Implantable cardioverter-defibrillators (ICD's), encapsulated in a conductive housing or enclosure, are generally implanted in the left pectoral region of a patient and electrically connected to the heart with one or more electrode carrying leads. One lead includes at least one set of electrodes positioned in the right ventricle. An arrhythmia detector detects ventricular arrhythmias, such as ventricular fibrillation. When such an arrhythmia is detected, a pulse generator delivers a defibrillation output pulse from the defibrillation electrode in the right ventricle to the conductive housing to terminate the arrhythmia.

Electrodes in the leads connected to the ICD may be positioned throughout the heart and attached to the tip of a lead or along the body of the lead. The electrodes are the components of the lead where the electrical current generated in the ICD is applied to the tissue of the patient.

SUMMARY

Embodiments include a tip electrode with a set of grooves or cut out regions to allow elution of a medical compound housed within the tip. The grooves and cut out regions in the tip electrode also promote edge effects in applying a shock to the adjacent tissue. The edges in the tip electrode focus the current streams resulting in lower threshold current levels for carrying out therapy such as pacing, defibrillation and cardioversion. The cut out regions also allow for tissue in-growth to minimize displacement of the tip. The cut out regions and grooves may be spaced apart to maintain the structural integrity of the electrode tip. The electrode tip may be hollow allowing a guidewire or stylet to pass through or partially through the electrode tip.

The electrode tip may be joined to or integrally formed with a weld electrode that is disposed at least partially within a body of the lead. The weld electrode connects the tip electrode to the wiring leading to the implantable cardiac device. The weld electrode is also mounted in the lead body and is hollow to allow for the passage of a guidewire or stylet through the weld electrode. The medical compound may be situated between the weld electrode and the tip electrode.

BRIEF DESCRIPTION OF THE DRAWINGS

Embodiments of the invention are illustrated by way of example and not by way of limitation in the figures of the accompanying drawings in which like references indicate similar elements. It should be noted that references to "an" or "one" embodiment in this discussion are not necessarily to the same embodiment, and such references mean at least one.

FIG. 5 is a diagram of another embodiment of a tip electrode.

FIG. 6 is a diagram of a further embodiment of a tip electrode.

Figure 1:
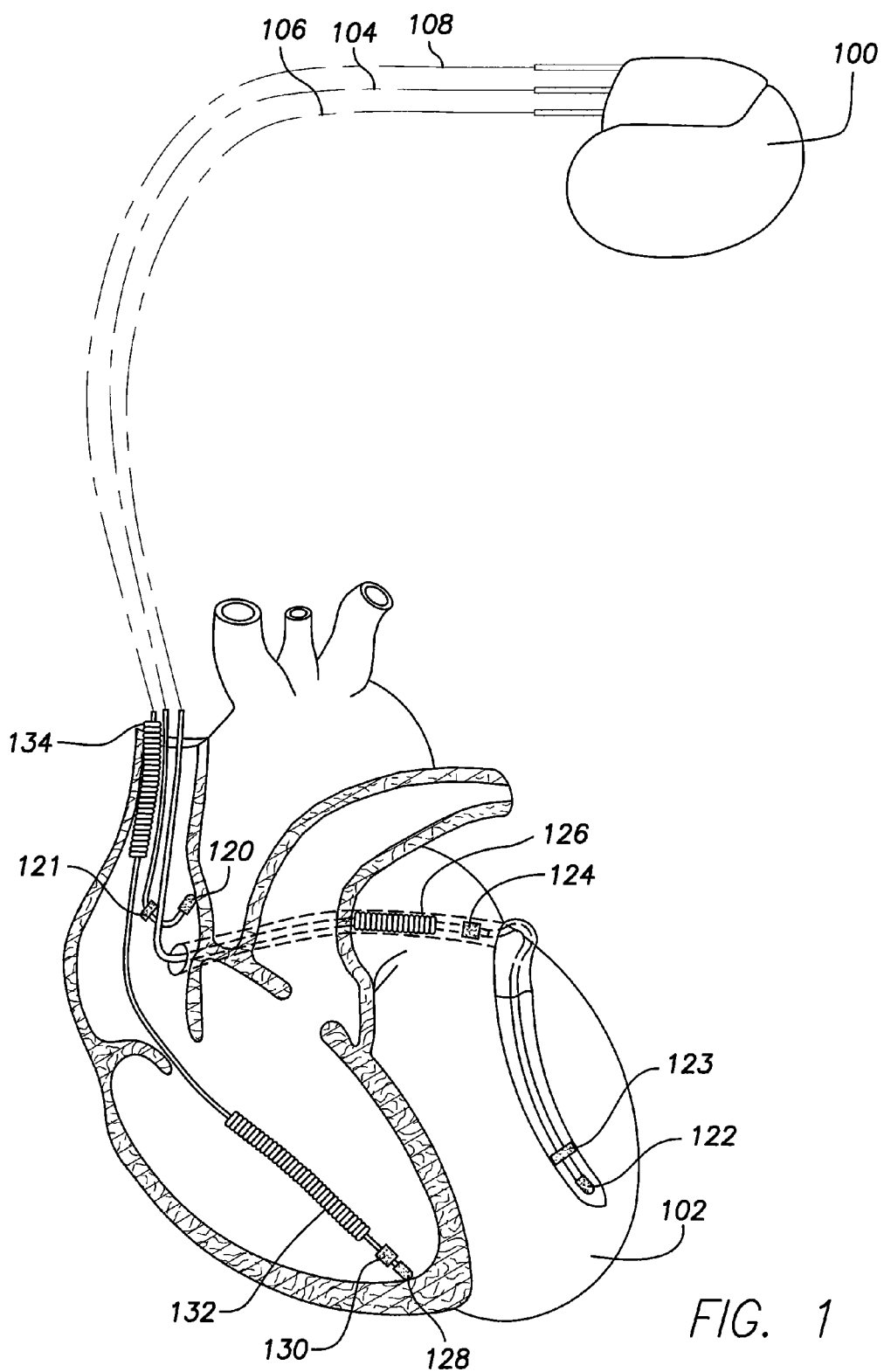
FIG. 1 is a simplified diagram illustrating an implantable stimulation device in electrical communication with leads implanted into a patient's heart for delivering multi-chamber stimulation and shock therapy.

In accordance with common practice, the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Also, like reference numerals denote like features throughout the specification and figures.

DETAILED DESCRIPTION

The invention is described below, with reference to detailed illustrative embodiments. It will be apparent that the invention may be embodied in a wide variety of forms, some of which may be quite different from those of the disclosed embodiments. Consequently, the specific structural and functional details disclosed herein are merely representative and do not limit the scope of the invention.

The following description sets forth but one exemplary stimulation device that is capable of being used in connection with the various embodiments that are described below. It is to be appreciated and understood that other stimulation devices, including those that are not necessarily implantable, can be used and that the description below is given, in its specific context, to assist the reader in understanding, with more clarity, the inventive embodiments described herein.

FIG. 1 shows an exemplary stimulation device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having, for example, an atrial tip electrode 120, which typically is implanted in the patient's right atrial appendage or septum. FIG. 1 shows the right atrial lead 104 as having an optional atrial ring electrode 121.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy or fibrillation shocks using, for example, a left ventricular tip electrode 122, left ventricular ring electrode 123, left atrial pacing therapy using, for example, a left atrial ring electrode 124, and shocking therapy using, for example, a left atrial coil electrode 126 (or other electrode capable of delivering a shock). For a complete description of a coronary sinus lead, the reader is directed to U.S. Pat. No. 5,466,254, "Coronary Sinus Lead with Atrial Sensing Capability" (Helland), which is incorporated herein by reference.

Stimulation device 100 is also shown in electrical communication with the patient's heart 102 by way of an implantable right ventricular lead 108 having, in this implementation, a right ventricular tip electrode 128, a right ventricular ring electrode 130, a right ventricular (RV) coil electrode 132 (or other electrode capable of delivering a shock), and superior vena cava (SVC) coil electrode 134 (or other electrode capable of delivering a shock). Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy or fibrillating shocks to the right ventricle.

Figure 2:
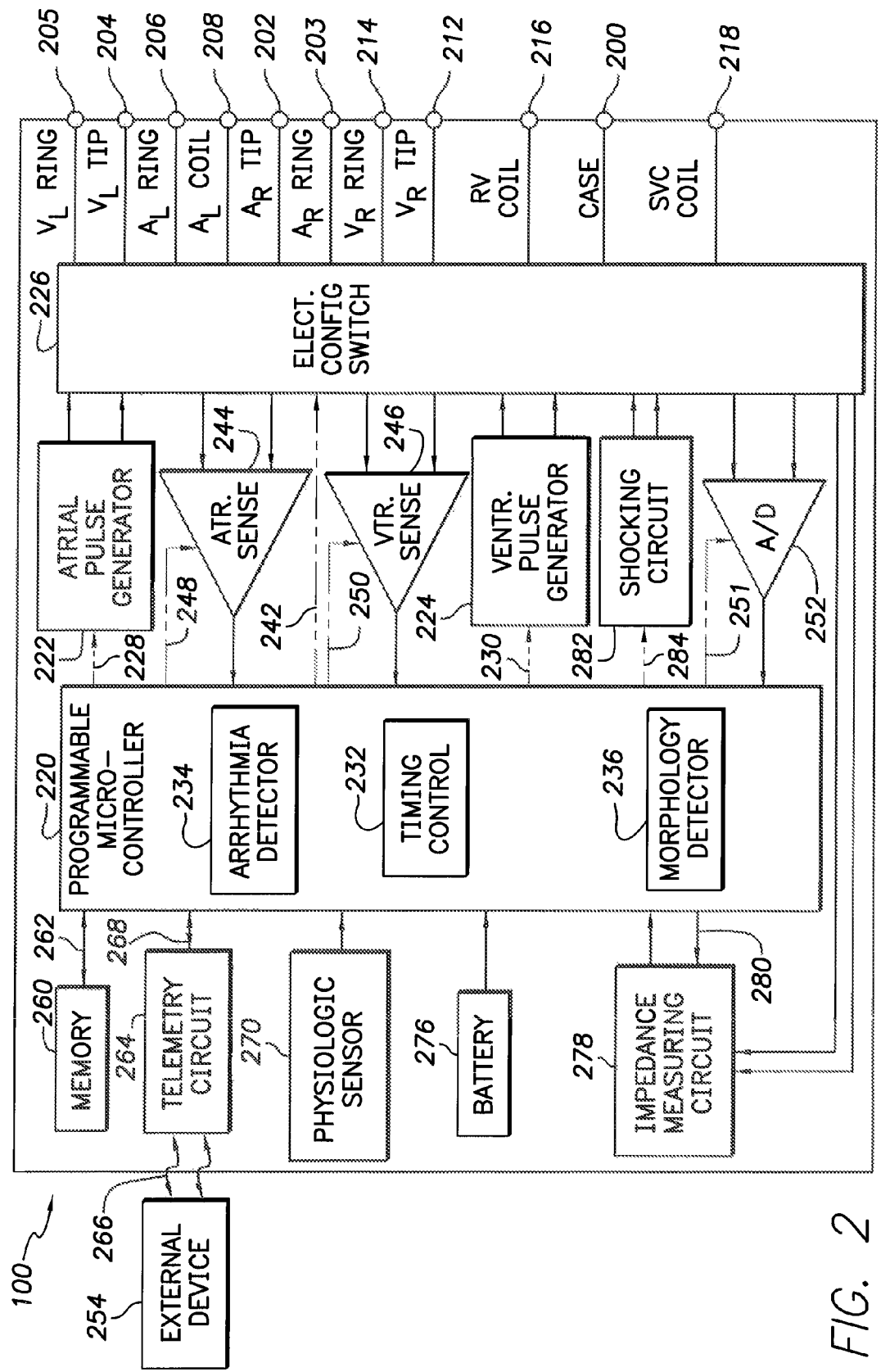
FIG. 2 is a functional block diagram of an implantable cardiac stimulation device embodying the present invention illustrating the basic elements thereof for providing cardioversion, defibrillation and pacing stimulation.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 203, 204, 205, 206, 208, 212, 214, 216, and 218 (shown schematically and, for convenience, the names of the electrodes to which they are connected are shown next to the terminals).

To achieve right atrial sensing and pacing, the connector includes, for example, a right atrial tip terminal (AR TIP) 202 adapted for connection to the atrial tip electrode 120. A right atrial ring terminal (AR RING) 203 may also be included adapted for connection to the atrial ring electrode 121. To achieve left chamber sensing, pacing, and shocking, the connector includes, for example, a left ventricular tip terminal (VL TIP) 204, left ventricular ring terminal (VL RING) 205, a left atrial ring terminal (AL RING) 206, and a left atrial shocking terminal (AL COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" refers to receiving an electrical signal or obtaining data (information), and "detection" refers to the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are classified by the arrhythmia detector 234 of the microcontroller 220 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured (e.g., via signal line 251) to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiologic sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses. While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

More specifically, the physiologic sensors 270 optionally include sensors to help detect movement and minute ventilation in the patient. The physiologic sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., for treatment, where the shock is in excess of 2 A, at voltages above 200 V, for periods of 10 seconds or more). The battery 276 also desirably has a predictable discharge characteristic so that elective replacement time can be detected. Accordingly, the device 100 preferably employs lithium or similar battery technology.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In one embodiment, the microcontroller 220 further controls a shocking circuit 282 by way of a control signal 284. The shocking circuit 282 applies shocking pulses using the stored energy of capacitors, the shocking pulses may be of low (e.g., up to 0.5 J), moderate (e.g., 0.5 J to 10 J), or high energy (e.g., 11 J to 40 J), as set by the microcontroller 220. Such shocking pulses are applied to the patient's heart 102 through, for example, two shocking electrodes, and as shown in this embodiment, may be selected from the left atrial coil electrode 126, the RV coil electrode 132, and/or the SVC coil electrode 134. As noted above, the housing 200 may act as an active electrode in combination with the RV electrode 132, and/or as part of a split electrical vector using the SVC coil electrode 134 or the left atrial coil electrode 126 (i.e., using the RV electrode as a common electrode). Any combination of electrodes may be used to apply a shock.

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In some embodiments device 100 also may include circuitry for processing signals from one or more pressure sensors. Depending upon the application, the pressure sensors may be implanted in the heart, in other locations in the patient such as the thoracic cavity, anywhere along a lead or within the housing 200.

Figure 3:
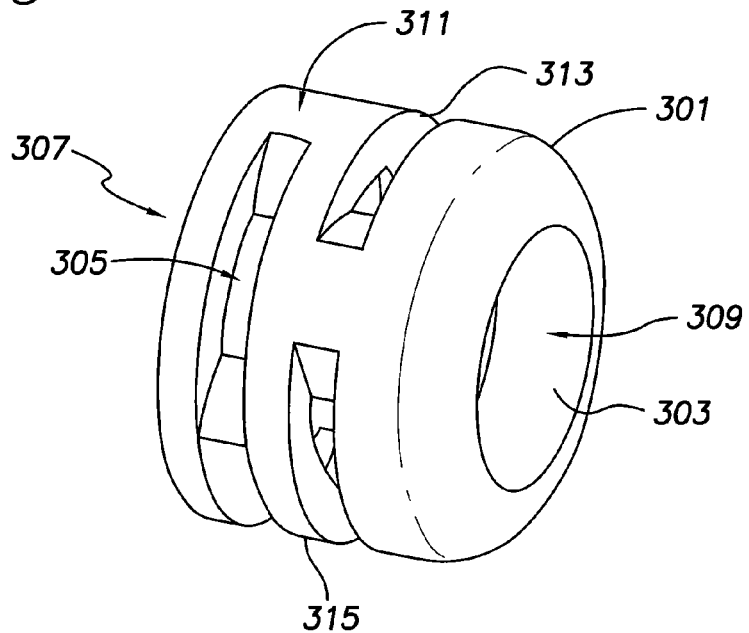
FIG. 3 is a diagram of one embodiment of a tip electrode.

FIG. 3 is a diagram of one embodiment of a tip electrode. A tip electrode 301 may be the contact component between a lead and the tissue of the heart, artery, vein or similar body structure in which a lead may be disposed. A current generated by the stimulation device passes into the patient at the tip electrode 301. The tip electrode 301 may be positioned at the end of a lead or at any point along a lead.

In one embodiment, a tip electrode 301 may have a generally annular shape. The diameter of the exterior surface of the tip electrode 301 may be 0.025 to 0.100 of an inch. In one embodiment, the diameter is 0.052 inches. The tip electrode 301 may define an interior space 309 that is substantially cylindrical. The tip electrode 301 may define an interior space of any shape including angular, squared, geometric, irregular or similar shapes. The diameter of the interior space 309 may range from 0.010 to 0.099 inches. The interior space 309 may form a conduit between a first port 303 at a distal end of the tip electrode 301 and a second port 307 at a proximal end of the tip electrode 301. The distal end of the tip electrode 301 may also have rounded edges to facilitate the advancement of a lead during an insertion process if the tip electrode 301 serves as the tip of the lead.

In one embodiment, the tip electrode 301 may include a sidewall 315 between the distal end and the proximal end. The sidewall 315 and the tip electrode more generally may have a wall thickness between 0.001 and 0.099 inches. In one embodiment, the thickness is 0.004 inches. The sidewall 315 may define an outer surface of the tip electrode 301. A set of grooves, notches or similar cut out regions 305, 313, may be defined by the sidewall 315 or outer surface of the tip electrode 301. The term set, as used herein, refers to any number or items including one item. In one embodiment, the cut out regions 305, 313 may be defined laterally, in relation to a central axis of the tip electrode 301. The cut out regions may have any depth up to the depth of the sidewall 315, thereby forming gaps or conduits through the sidewall 315. A cut out region may have a variable depth along its length. In one embodiment a cut out region may have a length substantially between 0.01 and 0.09 inches. For example, here the length may be up to 0.006 inches less than the diameter of the part. Thus, for a part diameter of 0.100 inches, the length may be 0.094 inches. In one embodiment, the length may be 0.046 inches. A cut out region may have a depth between 0.0001 inches up to the thickness of the sidewall 315. In one embodiment, the depth of the cut out regions may match a thickness of the walls at 0.004 inches. The cut out region may have a width between 0.001 and 0.009 inches. In one embodiment, the width may be 0.006 inches.

In one embodiment, multiple cut out regions may be formed in a sidewall 315. For example, multiple cut outs may be formed around a circumference of an annularly shaped sidewall 315. A space between the cut out regions may be between 0.001 an 0.090 inches. Multiple lines of cut out regions or different patterns of cut out regions may be formed in a sidewall 315. For example, cut out regions 305 and 313 may be staggered along a sidewall 315 to provide openings and conduits through the sidewall without significantly diminishing the structural integrity of the sidewall 315 and the tip electrode 301.

The dimensions of structures are provided herein are by way of example and the possible embodiments are not so limited. The number of cut out regions, size of cut out regions and spacing between the cut out regions may be varied, where the spacing of the cut out regions is greater and the size of the cut out regions smaller when the sidewalls are thin to maintain the integrity and strength of the tip electrode 301. Similarly, the space between cut out regions may be smaller and cut out regions larger if the sidewall of the tip electrode 301 is thicker. The size and shape may be dependent on intended use, generally, the smallest possible tip electrode with the thinnest walls permitted by manufacturing processes will be utilized.

In one embodiment, the cut out regions in the sidewall 315 may form a right angle or acute angle with the outer surface of the sidewall 315. These sharp edges improve the edge effects of the tip electrode 301. Sharp edges or points on the surface of the tip electrode 301 concentrate the current passing through the electrode and increases the density of the electrical field at that point. Concentrating the current through a narrow path or point lowers the threshold current level that must be generated at the stimulation device to effect a treatment, including defibrillation, cardioversion, pacing stimulation or similar therapy.

In one embodiment, one or more sections 311 of the sidewall between the cut out regions serve as weld points to join the tip electrode 301 to other structures through a weld or similar technique. For example, a tip electrode 301 may be welded to a structure within a lead such as a weld electrode.

In one embodiment, the tip electrode 301 may be manufactured by molding, extrusion, etching, machining, or similar process. For example, the tip electrode may be formed as a solid cylinder or in an annular shape and a cutting device may be used to create the cut out regions. The tip electrode 301 may be formed from a platinum iridium alloy, MP35N alloy, stainless steel or similar material with low resistance. In one embodiment, a platinum iridium alloy is used with 80% to 90% platinum. Any biocompatible material or combination of materials with a low resistance may be used to form a tip electrode 301.

In one embodiment, the tip electrode 301 may be covered with a coating such as titanium nitride (TiN), iridium oxide, or similar material that diminishes the polarization of the electrode to improve the sensitivity of the electrode for use in sensing applications.

Figure 4:
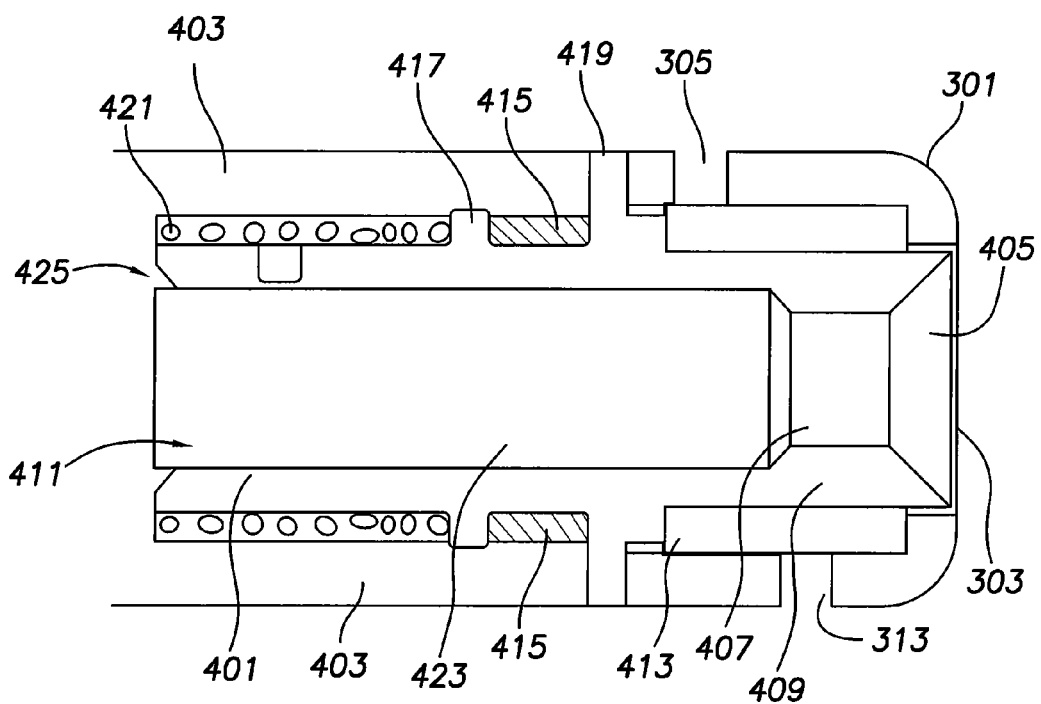
FIG. 4 is a diagram of one embodiment of a tip electrode attached to a weld electrode and disposed within a lead.

FIG. 4 is a diagram of one embodiment of a tip electrode 301 coupled to a weld electrode 401 disposed at the end of a lead body 403. In one embodiment, the tip electrode 301 is positioned coaxially around the weld electrode 401. The weld electrode 401 may define an interior space 423 having a first section 411 and a second section 407. The first section 411 may have an interior diameter of 0.010 to 0.099 inches. In one embodiment, the diameter may be 0.021 inches. The interior wall 409 of the second section 407 may be narrower than the first section 411. The diameter of the second section 407 may be 0.005 to 0.045 inches. In one embodiment, the diameter of the second section 407 may be 0.016 inches. The conduit defined by the first section 411 may narrow to the diameter of the second section 407 to prevent the advancement of a stylet or similar instrument through the interior conduit defined by the weld electrode 401. The diameter of the second section 407 may prevent the advancement of a stylet or similar instrument, while at the same time allowing the advancement of a guidewire or similar instrument. The ports at either end of the interior space 423 may be chamfered or beveled to assist in insertion of an instrument into the interior space 423 of the weld electrode 401. For example, the distal port 405 of the weld electrode 401 may widen to a point with the outer surface of the weld electrode.

In one embodiment, the weld electrode 401 may have a protrusion 419 or similar structure. The tip electrode 301 may be welded to the protrusion 419 to secure the tip electrode 301 to the weld electrode 401. In other embodiments a different engagement structure or technique may be used to secure the tip electrode 301 to the weld electrode 401.

In one embodiment, the weld electrode 401 may be disposed partially with a lead body 403. The weld electrode may have a protrusion 417 or similar structure to engage the lead body to secure the weld electrode 401 in relation to the lead body 403. For example, locking may occur between the lead body 403 and the weld electrode 401 in the recess distal to the protrusion 417. In another embodiment, any type of engagement structure may be used to secure the weld electrode 401 in relation to the lead body 403 including a form fit, snap fit, latch or similar mechanism.

In one embodiment, the lead body 403 may also be coupled to the weld electrode 401 by a secondary attachment mechanism such as a medical adhesive 415 or similar mechanism. For example, a medical adhesive 415 may be placed at the end of and under a lead body 403 to seal the end of the lead body 403 to the weld electrode 401 in the recess distal to the protrusion 417. In another embodiment, any type of biocompatible adhesive may be utilized.

In one embodiment, the lead 403 may be any type of lead attached to a stimulation device or similar device for implanting within a patient. The lead may be formed of silicon, polyurethane or similar biocompatible material. The lead 403 may include multiple tip electrodes 301 and weld electrodes 401. The lead 403 may utilize any type of mounting mechanism to hold a position in the body.

In one embodiment, the weld electrode 401 may be attached or in contact with a wire coil 421, cable or similar electrical conductor to provide electrical communication with the stimulation device. Electrical communication may include the transmission of data, power or similar electrical communication. The wire coil 421 may be attached by a weld, adhesive, form fit or similar technique. The wire coil 421 may be disposed in a space defined by the lead body 403 between the weld electrode 401 and the lead body 403. The wire coil 421 may run the length of the lead tying the weld electrode 401 and tip electrode 301 to the stimulation device circuitry. In one embodiment the wire coil 421 is welded to the protrusion 417. In other embodiments a different engagement structure or technique may be used to secure the wire coil 421 to the weld electrode 401.

In one embodiment, a medical compound 413 may be housed between the tip electrode 301 and weld electrode 401. The compound 413 may have a shape and size complementary to the interior space and interior surface of the tip electrode and complementary to the outer surface of the weld electrode 401. The medical compound 413 may be a matrix in a silicon rubber or similar material. For example, the compound may be a monolithic controlled release device containing a steroid such as dexamethasone phosphate or an anti-inflammatory agent such as dexamethasone acetate to control scarring around the tip electrode 301.

In one embodiment, the medical compound is exposed to the exterior environment around the tip electrode 301 through openings formed by the cut out regions (e.g., 305, 313) in the tip electrode 301. The openings in the tip electrode 301 allow for the eluting of the medical compound into the surrounding environment, tissues and body structures. The tissue and body structures surrounding the tip electrode 301 may grow into the cut out regions over time and at least partially secure the position of the tip electrode 301.

In one embodiment, the medical compound is shielded from the interior conduit defined by the outer wall of the weld electrode 401. The outer wall of the weld electrode 401 protects the medical compound from being impacted by a stylet, guidewire or similar instruments deployed through the weld electrode 401 and tip electrode 301. The weld electrode 401 may be formed from a platinum iridium alloy, MP35N alloy, stainless steel or similar material.

In one embodiment the proximal end of the weld electrode 401 may have a beveled portion. For example, a bevel 425 is depicted on the left hand side of the weld electrode 401 in FIG. 4.

FIG. 5 is a diagram of another embodiment of a tip electrode 501 with longitudinal cut out regions. The tip electrode 501 may have a substantially annular shape or similar shape. The tip electrode 501 may define an interior space that is cylindrical, angular, geometric, irregular or similarly shaped. The distal end 503 may define a first port 509. The distal end may also be rounded to aid during the insertion process. The proximal end may define a second port 507 allowing fluid communication through the tip electrode 501 from the first port 509 to the second port 507.

In one embodiment, the sidewall of the tip electrode 501 defines a set of cut outs 505 that run longitudinally and parallel to the central axis of the tip electrode. The depth of the cut out region 505 may vary along its length up to the thickness of the tip electrode. In one embodiment, the thickness of the tip electrode ranges from 0.001 and 0.099 inches. In one embodiment, the thickness is 0.004 inches. The length of the cut out regions may be 0.010 to 0.090 inches. In one embodiment, the length is 0.060 inches. The width of the cut out may be 0.001 to 0.009 inches. In one embodiment, the width is 0.006 inches. The length and width of the cut outs may vary individually.

FIG. 6 is a diagram of a further embodiment of a tip electrode 601. The dimensions of the tip electrode 601 may be similar to those of other embodiments. The tip electrode 601 may include a distal port 603, proximal port 607, connecting interior space 609 and a rounded distal end. The cut out may be in a helical pattern. The depth of the cut out region 605 may vary along the length of the cut out region. The depth may vary from 0.001 inches up to the thickness of the tip electrode 601. The space between the cut out regions may be uniform, patterned or irregular. The space may range from 0.005 to 0.009 inches. In one embodiment, the spacing may be 0.02 inches.

In view of the above, it should be understood that a stimulation device including leads and electrodes may be constructed using various combinations and modifications of the structures, components and processes described herein. For example, the structure, components and processes described in a given drawing may be used in a lead component or process described in another drawing.

In addition, the structures described herein may be implemented in a variety of ways. For example, the stimulation device described herein may be software executed by the microcontroller, firmware or an application specific integrated circuit. Also, the combinations of some of the components which are described herein as being "attached," "connected" "including," "affixed," etc., may be implemented as one or more integral components.

It should be appreciated that the applications discussed herein regarding various embodiments may be applicable to other uses and contexts as well. For example, the treatment component and processes described above may be utilized in treating other heart conditions. Different embodiments of the external monitoring and control systems described above may include a variety of hardware and software processing components. In some embodiments of the invention, hardware components such as controllers, state machines and/or logic are used in a system constructed in accordance with the invention.

In some embodiments, code such as software or firmware executing on one or more processing devices may be used to implement one or more of the described operations. The signals between sensors and external devices may take several forms. For example, in some embodiments a signal may be an electrical signal transmitted over a wire while other signals may consist of wireless signals transmitted through space. In addition, a group of signals may be collectively referred to as a signal herein. The signals discussed above also may take the form of data. For example, in some embodiments an application program of an external device may send a signal to another application program. Such a signal may be stored in a data memory.

The invention described herein may be used as part of an improved implanted cardiac device. While certain exemplary embodiments have been described above in detail and shown in the accompanying drawings, it is to be understood that such embodiments are merely illustrative of and not restrictive of the broad invention. In particular, it should be recognized that the teachings of the invention apply to a wide variety of systems and processes. It will thus be recognized that various modifications may be made to the illustrated and other embodiments of the invention described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. An implantable electrode comprising:
 a tip electrode defining a first conduit along a central axis of the tip electrode, the tip electrode defining at least one cut out region in a sidewall of the tip electrode, the sidewall extending from a proximal end of the tip electrode to distal end of the tip electrode, and the sidewall having a thickness of less than 0.010 inches;

a weld electrode coupled to the tip electrode, the weld electrode defining a second conduit along a central axis of the weld electrode;

the weld electrode extending between said proximal end and said distal end and defining an interior space concentrically located between an outer wall of the weld electrode and an inner wall of the tip electrode; and a medical compound disposed and secured within the interior space.

2. The implantable electrode of claim 1, wherein the second conduit has a first diameter in a first segment and a second diameter in a second segment, the second diameter being smaller than the first diameter.

* * * * *